(12) United States Patent
Cannon

(10) Patent No.: US 11,905,507 B2
(45) Date of Patent: *Feb. 20, 2024

(54) NETWORKED INCUBATOR OPERATION

(71) Applicant: Thrive Bioscience, Inc., Beverly, MA (US)

(72) Inventor: Howard Cannon, Boston, MA (US)

(73) Assignee: Thrive Bioscience, Inc., Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/179,493

(22) Filed: Mar. 7, 2023

(65) Prior Publication Data

US 2023/0203424 A1    Jun. 29, 2023

Related U.S. Application Data

(60) Continuation of application No. 17/401,225, filed on Aug. 12, 2021, now Pat. No. 11,634,682, which is a division of application No. 15/773,651, filed as application No. PCT/US2016/060722 on Nov. 4, 2016, now Pat. No. 11,118,154.

(60) Provisional application No. 62/250,986, filed on Nov. 4, 2015.

(51) Int. Cl.
*C12M 1/36* (2006.01)
*G16B 40/00* (2019.01)
*G16B 50/00* (2019.01)
*C12M 1/00* (2006.01)

(52) U.S. Cl.
CPC ............ *C12M 41/48* (2013.01); *C12M 1/005* (2013.01); *C12M 41/14* (2013.01); *G16B 40/00* (2019.02); *G16B 50/00* (2019.02)

(58) Field of Classification Search
CPC ...... C12M 1/005; C12M 41/48; C12M 41/14; G16B 40/00; G16B 50/00
See application file for complete search history.

(56) References Cited

U.S. PATENT DOCUMENTS

| | | | | |
|---|---|---|---|---|
| 8,383,395 | B2 * | 2/2013 | Hata | C12M 23/58 |
| | | | | 435/286.1 |
| 2011/0207209 | A1 * | 8/2011 | Hammons | C12M 23/42 |
| | | | | 435/297.1 |
| 2011/0263008 | A1 * | 10/2011 | Wang | C12M 41/00 |
| | | | | 435/288.7 |

(Continued)

OTHER PUBLICATIONS

International Search Report for PCT/US2016/060722, dated Feb. 9, 2017, 2 pages.

(Continued)

*Primary Examiner* — Shogo Sasaki
(74) *Attorney, Agent, or Firm* — Danielson Legal LLC

(57) ABSTRACT

Aspects of the present invention relate to a networked cell culture incubator and to methods for operating such an incubator. In one aspect, the cell culture incubator includes a network interface for communicating with a source of parameter data utilized successfully by other incubators. The incubator receives appropriate parameter data and conducts the incubation process as prescribed by the parameter data so as to provide an improved environment for cell culture growth. The incubator may share its own parameter data with the data source for use by other incubators. The incubator and data source may share other forms of data as well.

6 Claims, 8 Drawing Sheets

(56) References Cited

U.S. PATENT DOCUMENTS

| | | |
|---|---|---|
| 2014/0271571 A1 | 9/2014 | Magnant |
| 2015/0072871 A1 | 3/2015 | Kain et al. |
| 2015/0298123 A1 | 10/2015 | Block et al. |
| 2017/0145366 A1* | 5/2017 | Magnant ................ C12M 41/32 |
| 2020/0087607 A1* | 3/2020 | Magnant ................ C12M 41/12 |

OTHER PUBLICATIONS

Written Opinion for PCT/US2016/060722, dated Feb. 9, 2017, 5 pages.
Office action for U.S. Appl. No. 15/773,651, dated Jan. 6, 2021, 13 pages.

* cited by examiner

NETWORKED INCUBATOR OPERATION

CROSS-REFERENCE TO RELATED APPLICATIONS

The present application is a continuation of U.S. patent application Ser. No. 17/401,225, filed on Aug. 12, 2021, now issued as U.S. Pat. No. 11,634,682, on Apr. 25, 2023, which itself is a divisional application of U.S. patent application Ser. No. 15/773,651, filed on May 4, 2018, now issued as U.S. Pat. No. 11,118,154, on Sep. 14, 2021, which itself is the national phase of International (PCT) Patent Application No. PCT/US2016/060722, filed internationally on Nov. 4, 2016, and claims priority to and the benefit of provisional application No. 62/250,986, filed on Nov. 4, 2015, and is related to U.S. provisional applications No. 62/141,183, filed on Mar. 31, 2015; 62/141,187, filed on Mar. 31, 2015; 62/141,191, filed on Mar. 31, 2015; and 62/141,196, filed on Mar. 31, 2015, the entire disclosure of each of which is hereby incorporated by reference as if set forth in its entirety herein.

FIELD

Embodiments described herein relate generally to incubators, and in particular to cell culture incubators that can be configured to operate, at least in part, utilizing parameter data received through a network interface that may be gathered by at least one other incubator.

BACKGROUND

Cell culture incubators are used to grow and maintain cells from cell culture, which is the process by which cells are grown under controlled conditions. Cell culture vessels containing cells are stored within the incubator, which maintains conditions such as temperature and gas mixture that are suitable for cell growth.

Long-term cell culture is a useful technique in both research and clinical contexts. However, maintenance of long-term cell cultures, for example, long term cultures, tissue preparations, in vitro fertilization preparations, etc., in presently available cell incubators is a laborious process requiring highly trained personnel and stringent aseptic conditions. This high level of human involvement can introduce contaminants into the culture and cause shock from environmental changes, thereby lowering culture efficiency.

Accordingly, new types of cell culture incubators that provide a culture system with reduced human involvement are needed.

SUMMARY

This summary is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

Conventional cell culture incubators impose several barriers to productive long-term cell culture, particularly for purposes of maintaining cells for clinical purposes or for research purposes involving sensitive assays, e.g., for evaluating drug function or interrogating cellular function. For example, many presently available cell incubators require extensive operator interaction to load and unload culture plates, to move cell culture vessels, to supply sterilization medium, etc. Unfortunately, human operators introduce the possibility of human error, contamination, etc. Thus, the disclosure in part relates to a cell culture incubator that reduces human error by receiving parameter data controlling its operation derived from parameter data successfully used by other incubators.

According to one aspect of the disclosure, embodiments of the present invention relate to a non-transitory computer-readable medium having instructions stored thereon for performing a method of facilitating networked incubator operation. In some embodiments, the medium includes instructions operable on one or more processors for receiving, from a first networked incubator system, data that comprises incubator operating parameters for operating a networked incubator system; storing the received parameter data in a database; receiving a query for incubator operating parameters from a second networked incubator system; and transmitting, from the database in response to the received query from the second networked incubator system, parameter data that corresponds to the data received from the first networked incubator system and is arranged to control operation of the second networked incubator system.

In one embodiment, the received parameter data and the transmitted parameter data each comprise at least one of: an image, information derived from an image, a step in a process for incubator operation, temperature data, cell type data, time data, cell growth data, and growth medium data.

In one embodiment, the medium further includes instructions stored thereon for approving the query from the second incubator system prior to the transmission of parameter data.

In one embodiment, the non-transitory computer-readable medium further has instructions stored thereon for sending a query for parameter data to a server. In some embodiments, the non-transitory computer-readable medium has instructions stored thereon for sending authentication credentials in connection with a query for parameter data to a server.

In one embodiment, the medium further includes for anonymizing the received parameter data so that the first networked incubator system cannot be identified from the transmitted parameter data.

In one embodiment, the medium further includes instructions for computing values derived from the received parameter data. In one embodiment, the derived values are selected from the group consisting of compilations, statistics, and values that correspond to a deep learning network.

In one embodiment, the query received from the second networked incubator system comprises at least one of: an image, information derived from an image, a step in a process for incubator operation, temperature data, cell type data, time data, cell growth data, and growth medium data.

In one embodiment, the first networked incubator system and the second networked incubator system are the same networked incubator system.

According to another aspect, embodiments relate to a method of facilitating networked incubator operation. The method includes receiving, from a first networked incubator system, data comprising incubator operating parameters for operating a networked incubator system; storing, in a non-transitory memory, the received parameter data in a database; receiving, from a second networked incubator system, a query for incubator operating parameters; and transmitting parameter data from the database in response to the received query, the parameter data corresponding to the data received from the first networked incubator system and arranged to control operation of the second networked incubator system.

In one embodiment, the query received from the second networked incubator system includes at least one of: an image, information derived from an image, a step in a process for incubator operation, temperature data, cell type data, time data, cell growth data, and growth medium data.

In one embodiment, the received parameter data and the transmitted parameter data each comprise at least one of: an image, information derived from an image, a step in a process for incubator operation, temperature data, cell type data, time data, cell growth data, and growth medium data.

In one embodiment, the method further includes approving the query from the second incubator system prior to the transmission of parameter data.

In one embodiment, the method further includes anonymizing the received parameter data so that the first networked incubator system cannot be identified from the transmitted parameter data.

In one embodiment, the method further includes computing values derived from the received parameter data. In one embodiment, the derived values are selected from the group consisting of compilations, statistics, values that correspond to a deep learning network, etc.

In one embodiment, the query received from the second networked incubator system comprises at least one of: an image, information derived from an image, a step in a process for incubator operation, temperature data, cell type data, time data, cell growth data, and growth medium data.

In one embodiment, the first networked incubator system and the second networked incubator system are the same networked incubator system.

According to yet another aspect, embodiments of the present invention relate to a cell culture incubator system. The system includes a database; a first networked incubator in operable communication with the database, wherein the first networked incubator is configured communicate data regarding at least one operating parameter related to the operation of the first networked incubator; and a second networked incubator in operable communication with the database, wherein the second networked incubator is configured to receive data regarding the at least one operating parameter of the first networked incubator, and further configured to control operation of the second networked incubator based on the data regarding the at least one operating parameter.

In one embodiment, the data regarding the at least one operating parameter comprises at least one of: an image, information derived from an image, a step in a process for incubator operation, temperature data, cell type data, time data, cell growth data, and growth medium data.

In one embodiment, the second networked incubator further has instructions stored thereon for sending a query for parameter data to the database.

In one embodiment, the second networked incubator further has instructions stored thereon for sending authentication credentials in connection with a query for parameter data to a server.

According to yet another aspect, embodiments of the present invention relate to a method of facilitating networked incubator operation. In some embodiments, the method includes receiving, from a first networked incubator system, data comprising incubator operating parameters for operating a networked incubator system. In some embodiments, the method includes storing, in a non-transitory memory, the received parameter data in a database. In some embodiments, the method includes receiving, from a second networked incubator system, a query for incubator operating parameters. In some embodiments, the method includes transmitting parameter data from the database in response to the received query, the parameter data corresponding to the data received from the first networked incubator system and arranged to control operation of the second networked incubator system.

These and other features and advantages, which characterize the present non-limiting embodiments, will be apparent from a reading of the following detailed description and a review of the associated drawings. It is to be understood that both the foregoing general description and the following detailed description are explanatory only and are not restrictive of the non-limiting embodiments as claimed.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. Various embodiments of the invention will now be described, by way of example, with reference to the accompanying drawings, in which.

DETAILED DESCRIPTION

Figure 1:
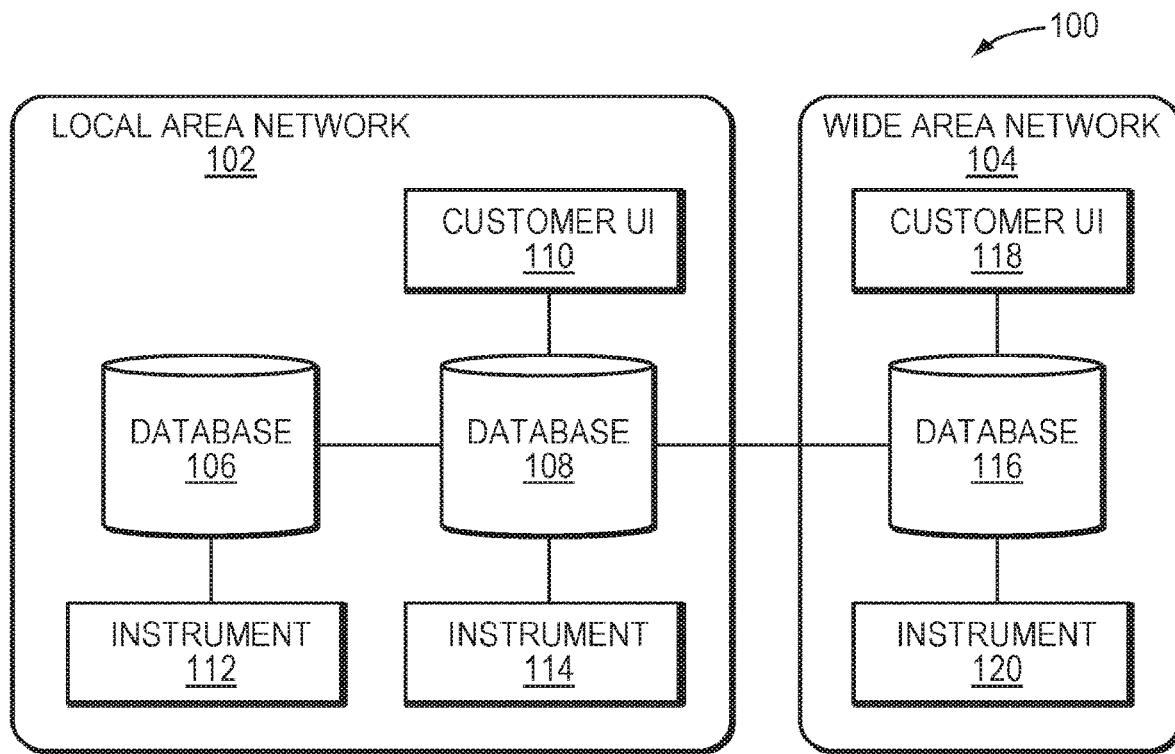
FIG. 1 illustrates the system architecture of networked instruments in accordance with one embodiment.

Aspects of the disclosure relate to automated incubators that enable productive long-term cell culture. It has been appreciated that, since traditional cell culture incubators require significant amounts of human intervention, the traditional incubation process is subject to myriad sources of error that can disrupt culture growth. For example, the mistaken introduction of items into an incubator by an operator from the external environment at the incorrect time or the incorrect stage of the incubation process can negatively affect the health or activity of a sample. Similarly, an operator's failure to follow the timing or order of steps specified by a protocol can kill a culture outright or invalidate the results of the culturing process.

According to one aspect, a cell culture incubator is equipped with a control system, a network interface, a non-transient storage, and one or more electrically controllable resources. These incubators may include a variety of such components, such as but not limited to sensors, environmental control systems, fluidics transport systems, robotics, etc., which may operate together at the direction of a computer, processor, microcontroller or other computing device. The control system controls the cell culture incubator and automatically monitors and adjusts cell culture conditions for optimal growth of the cell culture.

The control system can be programmed with a variety of protocols stored in the non-transitory storage medium, manually entered by an operator, or retrieved from an external data source using the network interface. Each protocol describes how the control system should operate the electrically controllable resources to incubate a particular cell line or culture. Each individual protocol will have its own duration, which may itself vary during execution, depending on the protocol's purpose.

Protocols may be shared directly among network-enabled cell culture incubators in a peer-to-peer arrangement or indirectly using, e.g., a hub-and-spoke type arrangement with a centralized repository or database. Protocols may also be stored for later reuse by the same network-enabled cell culture incubator. A protocol that is executed by one incubator may be manually or automatically associated with various metadata describing various aspects of the protocol, including but not limited to incubator type, cell type, date of run, time of run, whether the run concluded successfully, conditional steps performed by the run, etc., to facilitate future storage, retrieval, indexing, and search. The association of a protocol with various items of metadata may itself be semi-automated by copying some or all of the metadata associated with a similar protocol.

As a protocol executes, a variety of systems may collect various forms of data concerning the execution of the protocol. Examples of collected data include ambient environmental data (temperature, gas levels, humidity, etc.), sampled sensor data (pH; images of cells, wells, etc., using various imaging modes at various resolutions, etc.), values derived from image data (e.g., cell proliferation estimates, cell morphology, stem cell colony growth, etc.), other raw and processed data (e.g., flow cytometry, various other assays), and additional protocol-related data (which parts of the incubator are used, when they are used, how long they are used for; what volume of liquids are dispensed, when they are dispensed; bar code scans of various plates and consumables as they move through the incubator, etc.).

This data may be associated and directly or indirectly shared with other incubators in the same manner that protocols and metadata are shared, as discussed in greater detail below. As with protocols, each data set may be manually or automatically associated with various metadata describing various aspects of the data set, including but not limited to incubator type, cell type, date of run, time of run, whether the run concluded successfully, conditional steps performed by the run, protocol executed, protocol parameters used, instruments used, instrument components used, etc., to facilitate future storage, retrieval, indexing, and search. The data collection processes may be automated, e.g., by the protocol, manually specified, or both. The association of a data set with various items of metadata may itself be semi-automated by copying some or all of the metadata associated with a similar data set.

One or more control systems may be interconnected by one or more networks in any suitable form, including as a local area network (LAN) or a wide area network (WAN) such as an enterprise network or the Internet. Such networks may be based on any suitable technology and may operate according to any suitable protocol and may include wireless networks, wired networks, or fiber optic networks.

The various methods or processes outlined herein may be coded as software that is executable on one or more processors that employ any one of a variety of operating systems or platforms. Such software may be written using any of a number of suitable programming languages and/or programming or scripting tools, and may be compiled as executable machine language code or intermediate code that is executed on a framework or virtual machine.

One or more algorithms for controlling methods or processes provided herein may be embodied as a readable storage medium (or multiple readable media) (e.g., a non-volatile computer memory, one or more floppy discs, compact discs (CD), optical discs, digital versatile disks (DVD), magnetic tapes, flash memories, circuit configurations in Field Programmable Gate Arrays or other semiconductor devices, or other tangible storage medium) encoded with one or more programs that, when executed on one or more computing units or other processors, perform methods that implement the various methods or processes described herein.

In various embodiments, a computer readable storage medium may retain information for a sufficient time to provide computer-executable instructions in a non-transitory form. Such a computer readable storage medium or media can be transportable, such that the program or programs stored thereon can be loaded onto one or more different computing units or other processors to implement various aspects of the methods or processes described herein. As used herein, the term "computer-readable storage medium" encompasses only a computer-readable medium that can be considered to be a manufacture (e.g., article of manufacture) or a machine. Alternatively or additionally, methods or processes described herein may be embodied as a computer readable medium other than a computer-readable storage medium, such as a propagating signal.

The terms "program" or "software" are used herein in a generic sense to refer to any type of code or set of executable instructions that can be employed to program a computing unit or other processor to implement various aspects of the methods or processes described herein. Additionally, it should be appreciated that according to one aspect of this embodiment, one or more programs that when executed perform a method or process described herein need not reside on a single computing unit or processor, but may be distributed in a modular fashion amongst a number of different computing units or processors to implement various procedures or operations.

Executable instructions may be in many forms, such as program modules, executed by one or more computing units or other devices. Generally, program modules include routines, programs, objects, components, data structures, etc., that perform particular tasks or implement particular abstract data types. Typically, the functionality of the program modules may be organized as desired in various embodiments.

Turning to the figures, FIG. 1 illustrates a system 100 of networked instruments in accordance with one embodiment. The system 100 may include one or more of an local area network 102 (LAN; e.g., an Intranet) and/or a wide area network 104 (WAN; e.g., the Internet). As can be seen, the LAN 102 and the WAN 104 may be in operable communication with each other.

The LAN102 may include databases 106 and 108. Although the LAN 102 is illustrated as including two databases, the LAN 102 may include any number of databases that may store a variety of types of data and in a variety of different formats.

The databases may or may not be in communication with user interfaces. For example, database 108 may be in operable communication with a customer user interface 110. The customer user interface 110 may allow users to query the databases for information such as data related to operation of one or more instruments. The customer user interface 110 may then present the information to the user.

The databases 106 and 108 may be in further communication with instruments 112 and 114, respectively. These instruments 112 and 114 may be a cell culture incubator device or any type of component included with or otherwise used in conjunction with an incubator device. Although the LAN 102 is illustrated as including two instruments, the LAN 102 may include any number of instruments. Additionally, a particular database may be in operable communication with any number of instruments.

The WAN 104 may also include one or more databases 116. The database 116 may be similar in configuration to databases 106 and 108. The database 116 may also be in operable communication with a customer user interface 118. The customer user interface may be similar in configuration to the customer user interface 110 of the LAN 102, and may allow a user to request and receive data stored in the database 116. The WAN 104 may also include or otherwise be in communication with one or more instruments 120. The instrument 120 may be similar in configuration to the instruments 112 and 114 of the LAN 102.

The customer user interfaces 110 and 118 may be any sort of interface that allows one or more users to input commands, data, queries, or other types of information that may relate to one or more instruments and operations. The customer user interfaces 110 and 118 may be configured as, for example and without limitation, PCs, laptops, mobile phones, tablets, smartwatches, or any other devices that may receive information from and present information to users. For example, users may input instructions for one or more instruments and/or receive data related to operation of one or more instruments.

Examples of output devices that can be used to provide a user interface include printers or display screens for visual presentation of output, and speakers or other sound generating devices for audible presentation of output. Examples of input devices that can be used for a user interface include keyboards and pointing devices, such as mice, touchpads, and digitizing tablets. In other examples, a computer may receive input information through speech recognition or in another audible format, through visible gestures, through haptic input (e.g., including vibrations, tactile and/or other forces), or any combination thereof.

The databases may be configured as structured or non-structured databases and may be located in an incubator's non-transitory storage or remotely in a network accessible storage (e.g., NAS, SAN, etc.). The databases may permit entire data sets, partial data sets, individual entries in a data set, or the like, to be retrieved using a specified index value or a range of values. The data sets may also be stored with a hosted service provided by, e.g., a web-accessible server, thereby enabling data set sharing among networked incubators.

Figure 2:
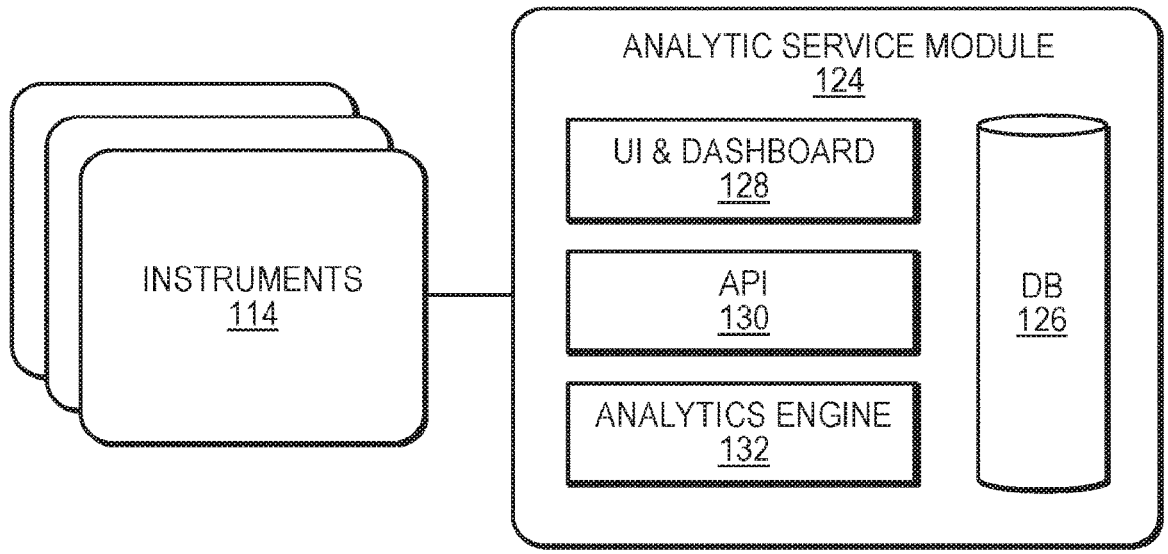
FIG. 2 illustrates multiple instruments of FIG. 1 in operable communication with an analytics module in accordance with one embodiment.

FIG. 2 illustrates an exemplary embodiment in which one or more instruments 114 are in operable communication with an analytic service module 124. The service module 124 may include or otherwise be in communication with a database 126 such as the databases 106, 108, or 116 of FIG. 1. The analytic service module 124 may further include a user interface and dashboard component 128, an application programming interface (API) 130, and an analytics engine 132.

In operation, the analytic service module 124 may issue commands to one or more instruments 114 regarding tasks to be performed. For example, a user such as a lab worker may input instructions via the user interface and dashboard 128 which are communicated to the appropriate instrument 114 via the API 130. The analytics engine 132 may gather, analyze, and present data regarding the instruments' operation in performing various assigned tasks. This data may be shared amongst other instruments and/or stored in the database 126. Accordingly, multiple instruments may communicate with each other and the analytics engine 132 may analyze, process, and communicate data regarding instrument operations. The instruments may be configured as cell culture incubators such as the one illustrated in FIG. 3. The cell culture incubator 200 may include an incubator cabinet 202 having a transfer chamber 220 and an internal chamber 230. An electrically controllable external door 212 opens and closes to permit communication between the transfer chamber 220 and the external environment (e.g. the environment external to the incubator cabinet 202). An electrically controllable transfer chamber door 214 opens and closes to permit communication between the transfer chamber 220 and the internal chamber 230.

The transfer chamber 220 and/or the internal chamber 230 may include one or more electrically controllable sensors for determining various internal conditions such as, but not limited to, temperature, humidity, gas content, pressure, and light levels. The transfer chamber 220 and/or the internal chamber 230 may include electrically controllable components for adjusting such internal conditions, such as a heater, humidifier, gas generator, air pump, etc.

In some embodiments, an electrically controllable transfer device is positioned within the internal chamber 230. In other embodiments, an electrically controllable transfer device may be positioned within the transfer chamber 220. In yet other embodiments, the transfer device is positioned in both the transfer chamber and the internal chamber. In other embodiments, the transfer device can freely move between the chambers (such as with a robot that can move between the chambers).

Figure 3:
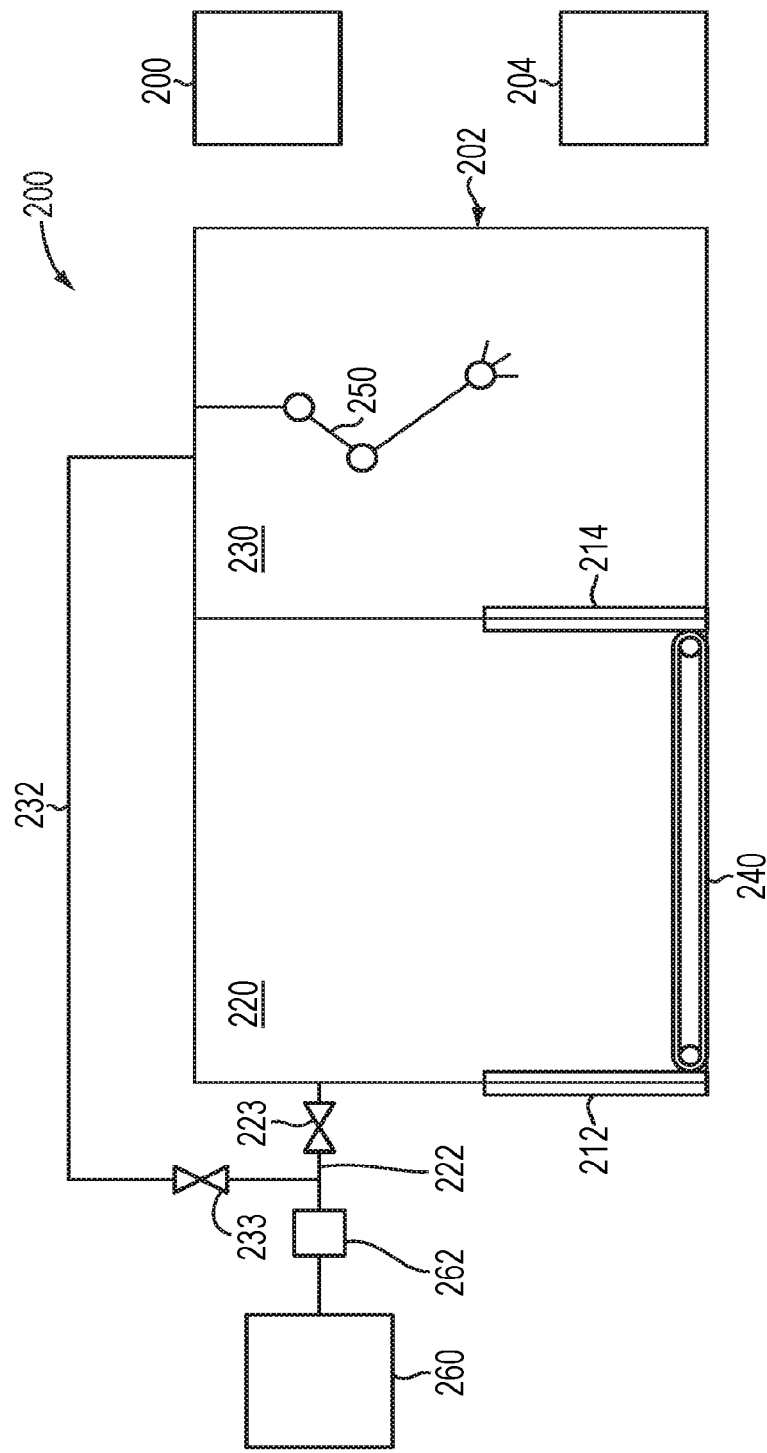
FIG. 3 is a schematic of an illustrative embodiment of a network-enabled cell culture incubator in accordance with one embodiment.

In the illustrative embodiment shown in FIG. 3, an electrically controllable transfer device 250 moves one or more items between the transfer chamber 220 and the internal chamber 230. The transfer device 250 may reach into transfer chamber 220, pick up one or more items from the transfer chamber 220, and move the item(s) into the internal chamber 230. The transfer device 250 may be a robotic arm or any other suitable transfer device described herein.

In some embodiments, more than one transfer device may be included in the cell culture incubator cabinet 210. In the illustrative embodiment shown in FIG. 3, in addition to the transfer device 250 of the internal chamber 230, an electrically controllable transfer device 240 is included in the transfer chamber 220. The transfer device 240 in this embodiment may be a belt conveyor system that conveys items from one end of the transfer chamber 220 to the other end of the transfer chamber 220. As one illustrative example, a computing unit 210 opens external door 212 and places an item on the transfer device 240. The computing unit 210 directs the transfer device 240 to convey the item towards transfer chamber door 214, which the computing unit 210 opens to receive the item. The computing unit 210 directs the robotic arm 250 of the internal chamber 230 to move the item off the transfer device 240 and to an appropriate location in the internal chamber 230. Alternatively, the item falls off the conveyor 240 as it approaches the end of the conveyor and lands in internal chamber 230. The computing unit 210 may move the item within the internal chamber 220 by a robotic arm 250 or other transfer device.

In some embodiments, one or more resources in an incubator cabinet and/or on a transfer device may be used by a computing unit 210 to locate and/or align the transfer device. In some embodiments, a location or alignment component may be a physical feature (e.g., one or more protrusions, indentations, guides, etc., or any combination thereof). In some embodiments, a location or alignment component may be electrically controllable by a computing unit 210, such as a signal and/or sensor (e.g., a laser, a camera, an ultrasonic range finder, etc., or any combination thereof).

It should be appreciated that other types of transfer devices may be used as part of the cell culture incubator 200. For example, in one embodiment (not shown), the cell culture incubator 200 includes a transfer device that includes an electrically controllable linearly actuated receptacle. In this embodiment, the transfer device includes a housing and a receptacle that is translated through the housing using an actuator that is electrically controllable by a computing unit 200. Using the actuator, the computing unit 210 moves the receptacle from one end of the device to the other end of the device. The receptacle can extend at least partially through a first opening at the first end of the transfer device and through a second hole at the second end of the device.

In yet another embodiment (not shown), the transfer chamber 220 includes an additional electrically controllable robotic arm type transfer device. It should be appreciated that any number and any type of transfer devices may be included in an incubator (e.g., within one or more chambers of an incubator cabinet). These transfer devices may vary in size and configuration as well.

As described herein, a computing unit 210 may control a sterilization process within transfer chamber 220 to sterilize any items added into the transfer chamber 220 from the external environment. In one embodiment, a sterilization medium is used as part of the sterilization process. Referring again to FIG. 3, an electrically controllable sterilization medium source 260 is in fluid communication with the transfer chamber 220. A pump 262 is used by a computing unit 210 to convey sterilization medium from the sterilization medium source 260 to the transfer chamber 220. Alternatively or in addition, the computing unit 210 may use the electrically controllable pump 262 to move sterilization medium from the transfer chamber 220 to the sterilization medium source 260. It should be appreciated that pump 262 may be integrated with the source 260 itself. In some embodiments, no pump is included at all.

In one embodiment, the sterilization medium used is ozone. However, it should be appreciated that other types of sterilization medium and corresponding source may be used other than ozone. As such, sterilization medium source 260 may be a source of any suitable sterilization medium.

The computing unit 210 may use the sterilization medium provided to the transfer chamber to sterilize the incubator cabinet or other parts of the incubator as part of a cleaning cycle. In one embodiment, during a cleaning cycle, sterilization medium provided by the source 260 is introduced by a computing unit 210 into the transfer chamber 220 to sterilize the chamber itself. The computing unit 210 may maintain the internal door 214 in a closed state to prohibit sterilization medium from entering internal chamber 230.

In another embodiment, a computing unit 210 sterilizes both the transfer chamber 220 and the internal chamber 230 utilizing various electrically controllable resources. During a cleaning cycle, the computing unit 210 may open the internal door 214 while ozone gas or other sterilization medium is generated or provided from source 260. With the internal door 214 open, sterilization medium may enter into both transfer chamber 220 and internal chamber 230.

With continued reference to FIG. 3, the computing unit 210 may directly route sterilization medium to internal chamber 230. The sterilization medium flow path includes one or more flow controllers 223, 233 (such as valves) that are used by the computing unit 210 to control the sterilization medium flow path. Flow controller 223 controls flow through a transfer chamber path 222 and flow controller 233 controls flow through an internal chamber path 232. In one mode, where sterilization medium is desired only in the transfer chamber 220, a computing unit 210 closes flow controller 233 while the computing unit 210 opens flow controller 223, and a computing unit 210 keeps the external door 212 and internal door 214 are closed. In another mode, where sterilization medium is desired only in the internal chamber, a computing unit 210 closes flow controller 223, opens flow controller 233, and closes internal door 214. In yet another mode, where sterilization medium is desired in both chambers, a computing unit 210 opens both flow controllers 223, 233 and closes external door 212. The computing unit 210 may open or close internal door 214 in this mode.

As depicted in FIG. 3, a computing unit 210 may be used to control one or more components of the cell culture incubator 200. For example, the computing unit 210 may control the sterilization medium source 260, pump 262 and/or 264, external door 212, internal door 214, transfer device 240, 250 and/or 270, sensors, and any components that affect the internal conditions of the incubator (e.g., heaters, humidifiers, gas generators, etc.). The computing unit 210 may be external to the incubator cabinet 202, as seen in FIG. 3. The computing unit 210 may receive information from one or more sensors located inside the incubator cabinet 210 (sensors may be in the transfer chamber 220 and/or the internal chamber 230). The computing unit 210 may communicate with one or more components of the cell culture incubator 210 and/or the sensors via wireless signals and/or wired signals.

As described herein, the computing unit 210 uses the electrically controllable resources of the incubator to provide and maintain appropriate temperature, and gas mixtures for cell growth. It should be appreciated that cell growth conditions differ for different cell types and that the incubators described herein can be programmed to maintain different conditions that are appropriate for each cell type.

In some embodiments, the computing unit 210 and the electrically controllable resources described herein monitor or assay culture media for nutrient depletion, changes in pH, changes in temperature, accumulation of apoptotic or necrotic cells, and/or cell density. In some embodiments, the computing unit 210 and the electrically controllable resources described herein are used to modify or change the culture media or conditions and/or to passage the cell cultures when appropriate. In some embodiments, these procedures are automated.

Other electrically controllable resources may include in various embodiments, for example, a liquid handling device (e.g., a pump, a pipettor, etc.), a delivery system for delivering culture vessels or other components to or from the incubator, an environmental control system for controlling the temperature, humidity, $CO_2$ concentration, barometric pressure, and other environmental aspects of the incubator, a door operation system, an imaging or detection system, and a cell culture assay system. In some embodiments, a means for detecting conditions in the medium is connected to or included in the incubator. In some embodiments, a processor is connected to or included in the incubator. In some embodiments, a non-transitory computer-readable medium is connected to or included in the incubator. The medium has instructions stored thereon operable on one or more processors to adjust the operation of the incubator system utilizing received parameter data.

In various embodiments, the electrically controllable resources of the incubator 200 may include, but are not limited to, one or more airlocks, doors, locks, interlocks, sterilizing means (e.g., $O_3$ generators, HO generators, heat, radiation, etc.), light sources, environmental control systems (controlling temperature, humidity, atmospheric gas composition, etc.), imaging systems (cameras, microscopes, holographic imagers, etc.), sensors (temperature, air purity, contaminant levels, pH, humidity, $N_2$, $CO_2$, $O_2$, $O_3$, HO, CO, light, meters, etc.), monitoring systems (oxygen monitors, carbon dioxide monitors, ozone gas detectors, hydrogen peroxide monitors, multi-gas monitors, etc.), filtration systems (fluid, gas, etc.), auxiliary systems (window wipers, controls, pumps, valves, apertures, etc.), positioning systems (laser light, wireless, etc.) and transfer devices (conveyor belt, robotic arms, etc.). For example, the airlock and doors may be opened or closed, all using various electrical signals issued by a computing unit 210, either directly by the unit or indirectly by an interface that adjusts the signals issued by the computing unit 210 to the voltages, currents, durations, protocols, etc., required to operate the resource.

In various embodiments each of these resources can be associated with an incubator (e.g., fitted within an incubator cabinet), incorporated as part of an incubator (e.g., attached to, integral to, or otherwise connected to an internal wall or door of an incubator), or positioned at a suitable location(s) outside or inside an incubator cabinet (e.g., within a transfer chamber and/or an internal chamber, for example attached to an internal wall, and/or upper or lower internal surface).

The above discussions regarding the incubator 200 relate to merely exemplary embodiments of the instruments shown in FIG. 1 and referred to throughout the application. Other types of devices may similarly be used in accordance with the various features of the invention.

Figure 4:
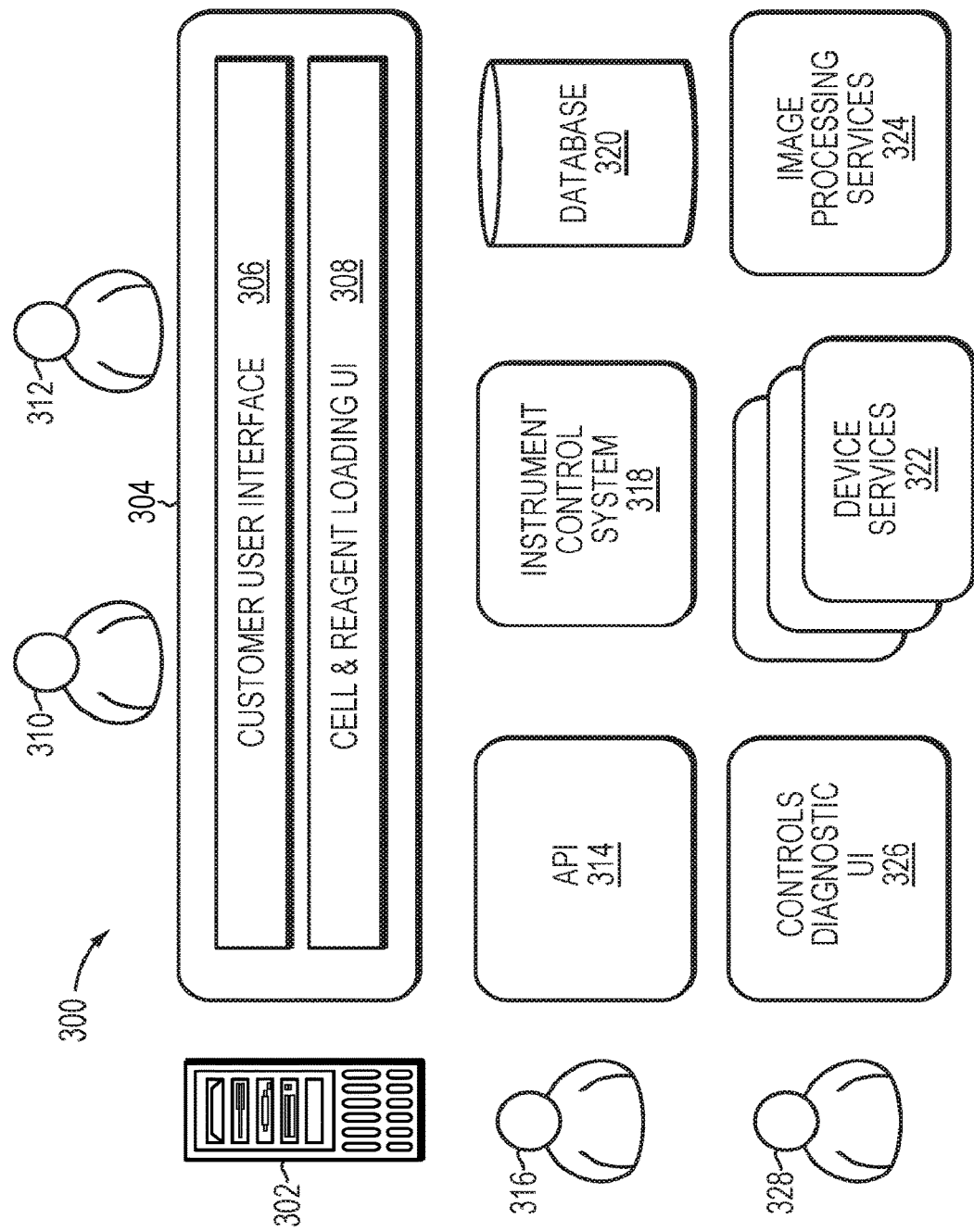
FIG. 4 illustrates a system that may be implemented on a network of FIG. 1 in accordance with one embodiment.

FIG. 4 illustrates a system 300 that may be implemented on network 102 or 104 of FIG. 1, for example. The system 300 may operate on or otherwise in conjunction with one or more servers 302 such as a laboratory information management system (LIMS) or an electronic lab notebook (ELN). The system 300 may include user interfaces 304 such as a customer user interface 306 and a cell and reagent loading user interface 308 that are accessible by one or more of scientists 310 and/or administrators 312.

The user interfaces 304 may be similar in configuration to the user interfaces of FIGS. 1 and 2. The user interfaces 304 may be in communication with an application programming interface 314 managed by a software engineer(s) 316 to at least communicate instructions to an instrument control system (ICS) 318. The ICS 318 may be in communication with one or more databases 320, and may issue commands/ instructions to one or more device services 322 (e.g., relating to incubators, refrigerators, etc.) and image processing services 324. The system 300 may also include a controls diagnostic user interface 326 accessible by a field service engineer 328. The controls diagnostic user interface 326 may allow the field service engineer(s) 328 to perform any maintenance, adjustments, or configurations to the various hardware devices.

In various embodiments, control of the operations of a cell culture incubator by the instrument control system 318 may be implemented using hardware, software, or a combination thereof. When implemented in software, the software code can be executed on any suitable processor or collection of processors, whether provided in a single computing unit or distributed among multiple computing units. Such processors may be implemented as integrated circuits, with one or more processors in an integrated circuit component. A processor may be implemented using circuitry in any suitable format. A typical processor is an x86, x86-64, ARMv7 processor, and the like. In various embodiments, the ITC 318 controls various processes performed inside the incubator. For example, the computing unit may issue various signals controlling the operation or the state of various electrically-controllable resources contained in or in communication with the incubator (e.g., a manipulator, an imager, a fluid handling system, etc.). In some embodiments, the ITC 318 controls imaging of cell cultures, picking of cells, weeding of cells (e.g., removal of cell clumps), monitoring of cell culture conditions, adjustment of cell culture conditions, tracking of cell culture vessel movement within the incubator, and/or scheduling of any of the foregoing processes.

In various embodiments, the ITCs 318 operate each of the electrically controllable resources in an "open loop" fashion, i.e., without feedback concerning the operation of the resource. For example, the computing unit may operate (i.e., enable, disable, actuate, etc.) each resource according to a pre-programmed schedule without accounting for the effect of the operation.

In various embodiments, the ITCs 318 may also operate a resource in a "closed loop" fashion utilizing an appropriate input (e.g., value, signal, etc.) from a sensor or other monitoring system. For example, the environment of the incubator may be modulated or controlled based upon information provided by one or more sensors. If an ITC 318 detects via a $CO_2$ sensor that the level of $CO_2$ in an incubator is lower than that required by an executing protocol, then the computing unit may issue a signal to a $CO_2$ source to increase the level of $CO_2$ in the incubator until the sensor indicates that the desired concentration of $CO_2$ has been achieved. The same is true of, e.g., oxygen, humidity, etc., and any other parameter in the incubator that is subject to adjustment utilizing one of the electrically controllable resources.

The ITC 318 may take any of a number of forms, such as a rack-mounted computer, a desktop computer, a laptop computer, a tablet computer, an embedded computer, a next unit of computing (NUC), etc., integrated into the incubator or external to the incubator and communicating with via a wired or wireless interface (e.g., gigabit Ethernet, 802.11x, etc.). Additionally, the ITC 318 may be a component not generally regarded as a computer but capable of executing software providing appropriate functionality, such as a Personal Digital Assistant (PDA), a smart phone or any other suitable portable, mobile or fixed electronic device, including the incubator itself.

Figure 5:
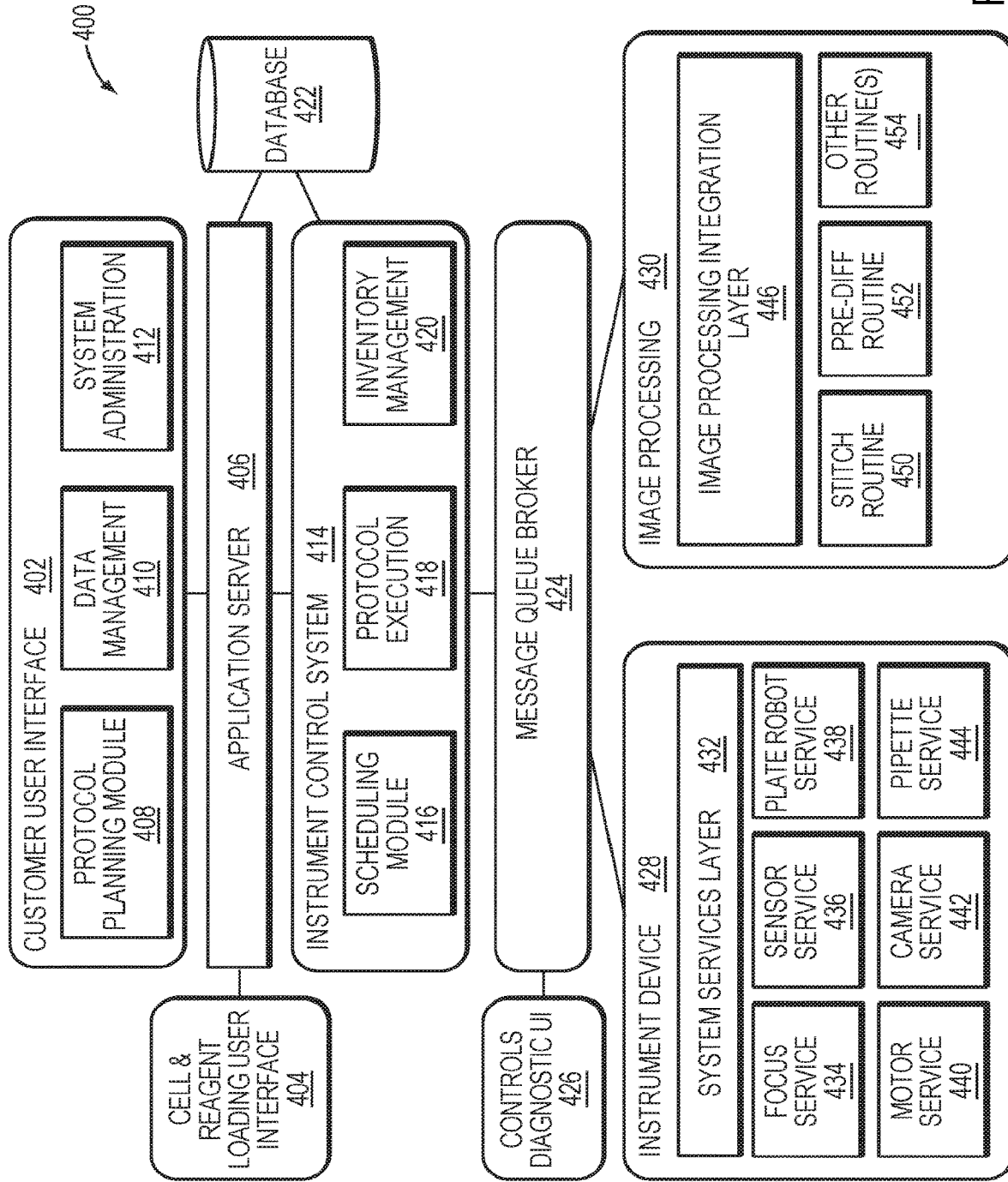
FIG. 5 illustrates the components of FIG. 4 in accordance with one embodiment.

FIG. 5 illustrates a networked system 400 such as the system 300 of FIG. 3 in more detail. The system 400 may include at least one customer user interface 402 and at least one cell and reagent loading user interface 404 in communication with an application server 406. The customer user interface 402 may be accessible by a user and similar in configuration to the customer user interfaces of FIG. 1. The customer user interface 402 may include various modules relating to operation of the incubators such as, but not limited to, a protocol planning module 408, a data management module 410, and a system administration module 412.

The protocol planning module 408 may allow a user to, via the customer user interface 402, plan various protocols to be implemented by an instrument. The customer user interface 402 may similarly present data or other types of information regarding instrument operation.

The data management module 410 may perform tasks related to the development, execution, and management of various policies and procedures required to appropriately manage data of the system 400.

The system administration module 412 may perform tasks related to or otherwise enable an administrator to configure and maintain operation of the various components of the system 400.

The customer user interface 402 may query the application server 406 regarding instrument status and/or to send commands. These queries and instructions may be communicated via web socket communication protocols.

The cell and reagent loading user interface 404 may also be in communication with the application server 406. The cell and reagent loading user interface 404 may communicate with the application server 406 via web socket communication protocols, and may be separate from the customer user interface 402 because they're intended for different purposes. The cell and reagent loading user interface 404 may be configured as a tablet as part of or otherwise under the hood of a cell culture lab. Accordingly, the cell and reagent loading user interface 404 may therefore facilitate the creation and labeling of plates with cells within the lab.

The application server 406 may subsequently publish commands or instructions to the internet control system (ICS) 414. The ICS 414 may be similar to the ICS 318 of FIG. 4. The application server 406 may communicate these commands or instructions to the ICS 414 via web socket communication protocols and/or via the advanced message queuing protocol (AMQP).

Instructions may be communicated to the ICS 414. The ICS 414 may be in charge of passing along various instructions to an instrument (e.g., an incubator) regarding the instrument's operation. The ICS 414 may include a scheduling module 416, a protocol execution module 418, and an inventory management module 420, among others.

The scheduling module 416 may schedule various electrically controllable resources so as to execute one or more protocols. In various embodiments, the scheduling module 416 accounts for the capabilities of the incubator, including the limited supplies of consumables (as communicated by the inventor management module 420), the dependency of later operations on the successful completion of early operations, the ability of the incubator to perform certain operations in parallel, the scheduled use of the incubator resources (e.g., transport resources) by another protocol, the satisfaction of certain conditions prior to execution, the time predicted for the completion of certain steps or operations of the protocol, etc.

The protocol execution module 418 may be configured to issue commands to various electrically controllable resources in accordance with instructions outputted by the scheduling module 416. The protocol execution module 418 may similarly monitor the execution of various protocols and receive data regarding their execution.

The inventory management module 420 may be configured to monitor the inventory of the incubator and lab environment. The inventory management module 402 may be configured to, for example, track the quantity of various lab equipment or samples throughout a given period of time. Data regarding the amount of resources may be communicated to the scheduling module 416 so that the scheduling module 416 can, based on the resources available at particular time, schedule certain protocols.

The application server 406 and the ICS 414 may also be in communication with one or more databases 422. The database(s) 422 may store data regarding system and instrument operation, and may be configured as a NoSQL database, for example. Also, data structures may be stored in computer-readable media in any suitable form. Non-limiting examples of data storage include structured, unstructured, localized, distributed, short-term and/or long term storage. Non-limiting examples of protocols that can be used for communicating data include proprietary and/or industry standard protocols (e.g., HTTP, HTML, XML, JSON, SQL, web services, text, spreadsheets, etc., or any combination thereof). For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

The ICS 414 may publish commands and receive data regarding events using AMQP, for example. The message queue broker 424 essentially allows for the various services of the instrument device 424 (discussed below) to intercommunicate. The message queue broker 424 may also be in communication with a controls diagnostic user interface 426. Similar to the ICS 414, the controls diagnostic user interface 426 may publish commands and receive data regarding events using AMQP. The controls diagnostic user interface 426 may be accessible by, for example, one or more field service engineers to enable them to perform any required maintenance on the instrument or instrument components.

The instrument device 428 may include a system services layer 432 to control the various modules 434-444 related to instrument operation. These modules may include, but are not limited to, a focus service module 434 for focusing one or more sensors; a sensor service module 436 for operating one or more sensor devices; a plate robot service module 438 for operating a plate robot; a motor service module 440 for operating one or more motors; a camera service module 442 for operating one or more cameras; and a pipette service module 444 for operating one or more pipettes.

In other words, the instrument device 428 may host the various services that are capable of driving the various hardware components. These services can be configured to execute at various levels of complexity. For example, a simple service may involve focusing a camera. A more complex service may involve multiple components, such as movement by several motors. Various components may of course receive instructions from different services. For example, a pipette can listen to commands from the motor service 440 and the pipette service 444. Accordingly, a single hardware device can belong or otherwise listen to multiple services.

The instrument device 428 therefore comprises two aspects. First, the hardware aspect, which includes various devices of the incubator. Second, the logical aspect, which comprises the various services that enable the hardware to operate and perform various tasks.

The image processing module 430 may include an image processing integration layer 46 to control the various modules 450-454 that are related to image processing. Certain tasks may require the analysis of multiple images collected over multiple time frames. Accordingly, this may require coordination amongst various modules. These may include a stitch routine module 444 that may be used to stitch images (e.g., images of samples) together.

The pre-differential module 452 may be used to detect discrepancies between stem cells during cell development. For example, stem cells are generally programmed to develop into a certain type of cell. However, oftentimes cells develop differently than expected. These discrepancies in cells can spread to neighboring cells. Accordingly, the pre-differential module 452 may execute various novel algorithms to detect such discrepancies before they spread and impact neighboring cells.

Figure 6:
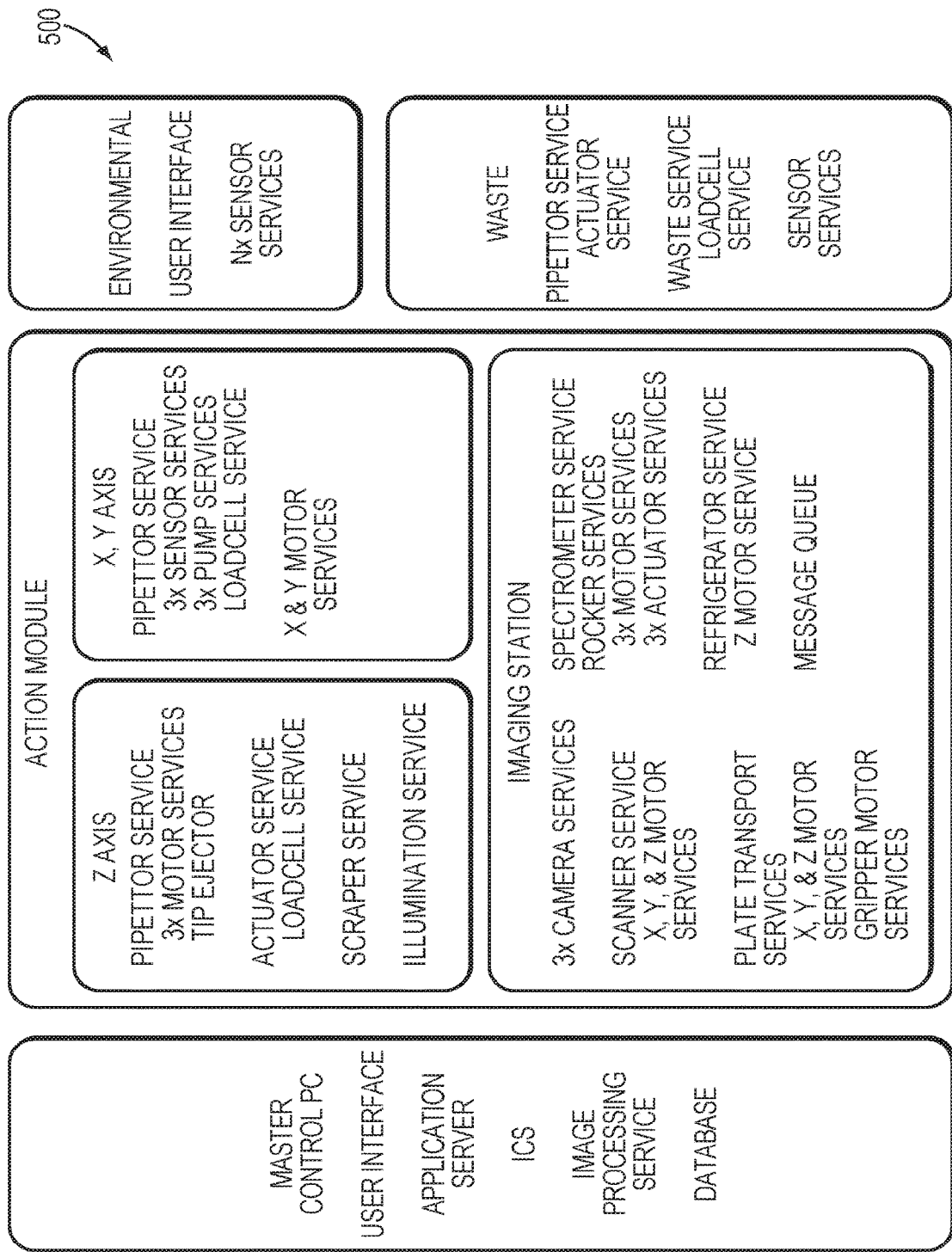
FIG. 6 illustrates various services in accordance with one embodiment.

These types of imaging-related modules are merely exemplary. Accordingly, it is contemplated that other modules configured to execute algorithms relating to image processing and analysis may be included, and may depend on the particular task. For example, FIG. 6 gives an overview of several different types of services 600 that may be used in conjunction with different components and for different tasks. These services may be in communication with a master control 602, which may include components such as a user interface, application server, ICS, image processing service module, and one or more databases.

The action module 604 may include services related to movement and operation of various devices of the incubator. For example, one or more pipettor services can be used to control movement of a pipette in the Z, X, and Y axes. Additional services that relate to pipette operation may include motor one or more motor services and actuator services to control movement of the pipette in various directions, one or more sensor services to gather information regarding the environment surrounding a pipette, one or more pump services to control liquid flow, and one or more scraper services to interact with a sample.

The action module 604 may also include services relating to image procurement and analysis. These may include camera services to control operation of cameras (e.g., to focus one or more cameras), scanner services to control scanners, plate transport services to control motions of plates (i.e., by operating one or more motors in various axes), gripper services to control grippers of plate transports, refrigerator services to control one or more refrigerators (and a motor service to control movement of a refrigerator), and a message queue service to receive and manage messages. The action module 604 may also include one or more services related to managing to the chain of possession of samples as well as services to verify digital signatures of incoming messages.

The environmental module 606 may gather data regarding the incubator's environment. For example, to gather environmental information, an incubator device may include a user interface and a plurality of sensor devices controlled by a plurality of sensor services to capture data regarding temperature, $CO_2$, $O_2$, pressure, etc.

The waste module 608 may include services related to waste management. For example, the waste module 608 may include a load cell service, actuator services, and sensor services to help detect and move waste.

Referring back to FIG. 3, the network interface 204 permits the incubator 200 to communicate with other network-connected devices, such as incubators, computers, network-enabled data sources, etc. The communications may include transmitted and received messages, the messages including but not limited to shared data concerning protocols, protocol runs, protocol parameters, etc. The network interface 204 may also be configured to communicate one or more digital signatures to verify the authenticity of files or messages transferred between instruments.

The network interface 204 of each instrument may also gather data regarding analyzed samples. For example, features of various embodiments of the present invention may include chip cards for storing data on cells leaving/entering a particular incubator. For example, a smart card may be configured on a plate and could be read by a system or incubator receiving that plate. Accordingly, this may act as a "check in" and "check out" system that monitors a particular plate and helps preserve the chain of custody of the plate.

Transmitting shared data to other network-connected devices enables those devices to re-share the data to other incubators or analyze the shared data, in particular image data. Receiving shared data permits the incubator(s) 200 to improve how they operate their protocols, make recommendations concerning operations to the operator of the incubator 200, etc.

Figure 7:
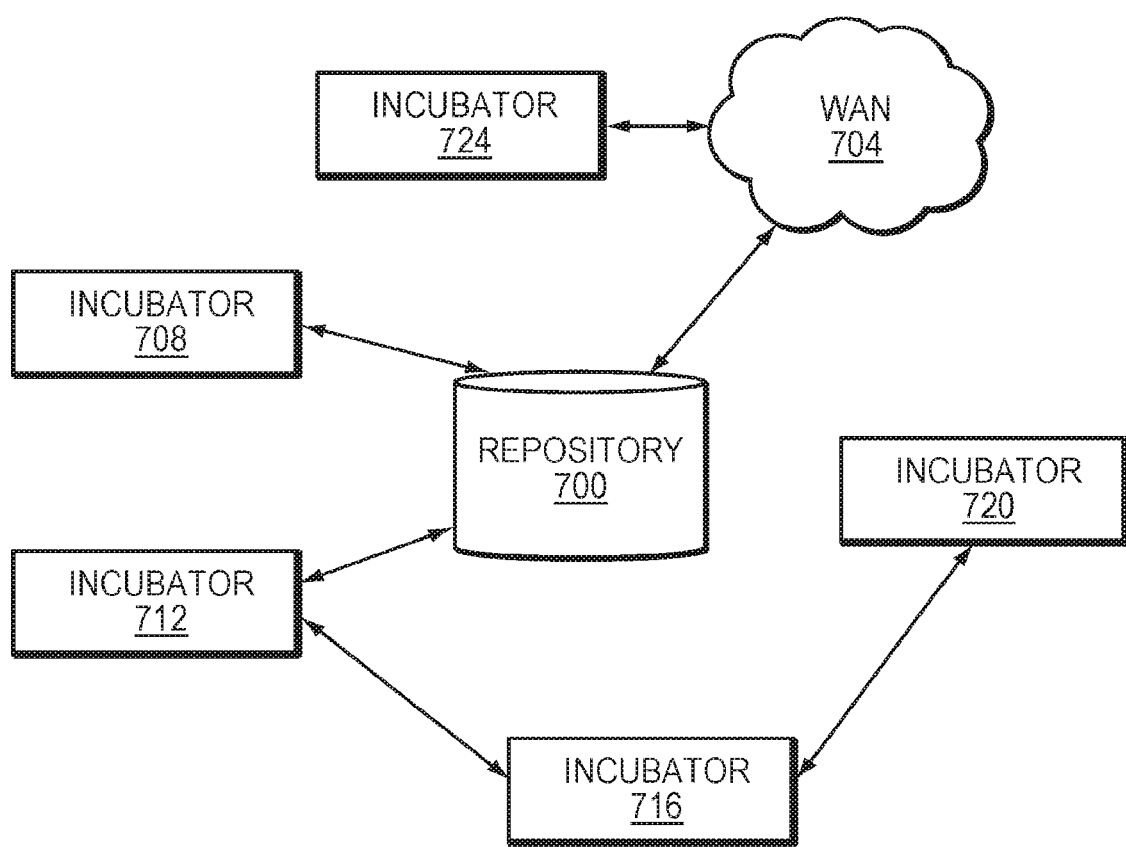
FIG. 7 illustrates a plurality of network-enabled cell culture incubators interoperating in accordance with one embodiment.

FIG. 7 depicts a plurality of network-connected incubators 708-724, such as the incubator of FIG. 3, interacting so as to share various data sets, including but not limited to protocol, protocol results, associated metadata, etc. Sharing data sets permits individual incubators to share protocols, improve protocol operations, make recommendations to individual human operators concerning protocol execution, reanalyze prior runs, etc. Each incubator may also store its own protocols and data sets for later reuse by that same incubator (not shown).

In some embodiments, the incubators 708-724 may be interconnected with other incubators and or network accessible data stores via LAN or WAN. The incubators may transmit various shared data sets (protocols, parameters, results, other metadata, etc.) to other incubators or these data stores to facilitate study and reuse of these data sets. The data stores may themselves share data sets to further facilitate study and reuse of the data sets.

As the data sets become more widely shared, either directly between incubators or indirectly using the data stores, individual incubators can use this shared data to improve protocol execution and outcomes. Individual incubators can rely exclusively on this shared data or utilize the shared data in combination with data local to the incubator, in some embodiments interacting with a plurality of shared data sources as if were a single shared data source.

The repository 700 may be a network-enabled data store, such as a NAS, SAN, network-enabled RAID array, web-hosted storage service (e.g., AWS), relational or object-oriented or other database, that permits data to be stored and retrieved by one or more devices using various network communications. Repository 700 is connected to one or more incubators (e.g., incubator 708) via local area network connections (e.g., Ethernet, Token Ring, etc.) and one or more incubators (e.g., incubator 724) via wide area network connections (e.g., Internet or WAN 704). The incubators may be the form of incubator illustrated in FIG. 3, or they may be a different form of incubator implementing a common protocol for data sharing and requests establishing compatibility with the incubators of FIG. 3. For example, the protocol may allow for the specification of various parameters that determine the data sets retrieved from a repository 700.

Incubator 708 is directly connected to repository 700, permitting incubator 708 to transmit various shared data sets to the repository 700 and retrieve various data sets from the repository 700 by providing a query with various parameters specifying the data sets of interest.

Incubator 712 is, like incubator 708, directly connected to the repository 700 and indirectly connected to incubator 508 by way of repository 700. Incubator 712 can transmit various data sets to the repository 700 and retrieve various data sets from the repository 700 by providing a query with various parameters specifying the data sets of interest. Incubator 712 can also transmit various data sets to the incubator 708 and retrieve various data sets from the incubator 708 by providing a query with various parameters specifying the data sets of interest to be relayed by repository 700.

Incubators 712, 716, and 720 are interconnected in a peer-to-peer configuration. This arrangement allows each of the incubators to share data sets with each other, transmitting data sets to and retrieving data sets from connected incubators as if one of the connected incubators is a repository. Since incubator 712 is also connected to repository 700, incubators 716 and 720 can communicate with repository 700 as well as repository-connected incubator 708.

Incubator 724 is connected to repository 700 via WAN 704, permitting incubator 724 to transmit various shared data sets to the repository 700 and retrieve various data sets from the repository 700 by providing a query with various parameters specifying the data sets of interest via the WAN 704.

Individual incubators can selectively choose the shared data that they receive or the received shared data that they use by specifying various selection parameters that may be relevant to the protocol presently executing (or to be executed) on the incubator. The shared data sets may be filtered to exclude those data entries that do not satisfy the relevant selection parameters.

The incubators 708-724 may utilize the shared data as it received or it may use various derived values thereof (e.g., statistical derivatives, compilations, deep learning networks, etc.) in the protocols that it executes. For example, a shared data set may detail the typical time it takes for a certain kind of cells to grow under certain conditions from their current state to requiring passaging, permitting a protocol to predict that the current culture of those cells will require passaging in, e.g., 10 hours, scheduling appropriate imaging and image analysis for that timeframe. If the current culture is not ready for passaging by that time, the operator may be alerted. If the imaging system indicates that the cells are fully disassociated in an unusual amount of time, the imaging system may reimage the culture, image a different area of the well, issue an alert to a user or another system, etc.

The incubators and/or shared data sources may use shared data sets from one incubator to reanalyze and reinterpret prior runs from the same or another incubator, especially images. Shared data sets may also be analyzed and used to recommend choices and options to an operator, e.g., which media to use for a particular cell line.

Protocols and data sets may be anonymized prior to sharing, making it difficult or impossible for third parties to determine the original source (i.e., author or incubator) of the protocol or the data set. The anonymization process may be performed by the original incubator prior to the transmission of the protocol or dataset, by the repository 700 hosting the protocol or the data set for sharing, etc.

Each protocol may include a variety of conditional actions, i.e., actions triggered upon the satisfaction of a particular condition. Examples of such conditions include, but are not limited to, a value meeting a particular value or falling within a particular range, the result of an automated or semi-automated analytical technique (e.g., image analysis, pH measurement, etc.), the result of a command received via a user interface from an operator, etc. In various embodiments particular values of interest include absolute time, relative time, elapsed time, etc. The threshold values or ranges of interest may be programmed in advance or derived in an automated manner from various data sets, such as previous runs of the protocol currently being executed, or other protocols executed in connection with the particular cell type of interest. Examples of such actions may include the operation of a particular piece of electrically controllable equipment; the execution of another protocol, such as a sub-protocol or a replacement protocol; the communication of various information to an operator or a computing unit. In various embodiments, a human operator or a computing unit may alter the stored protocol to address various operating conditions or constraints.

In some embodiments, information related to the operation of the incubator (e.g., temperature, humidity, gas composition, images, cell culture conditions, etc., or any combination thereof) can be obtained from one or more sensors associated with the incubator (e.g., located within the incubator cabinet, located within the incubator but outside the incubator cabinet, located in proximity to the incubator and in electrical communication with the incubator or an associated computing unit, etc.), and can be stored in computer-readable media to provide information about conditions during a cell culture incubation. In some embodiments, the computer-readable media comprises a database. In some embodiments, said database contains data from a single incubator. In some embodiments, said database contains data from a plurality of incubators. In some embodiments, data is stored subject to various security mechanisms and protocols that render it resistant to unauthorized access and manipulation. In some embodiments, all data generated by the incubator(s) and related facilities are stored. In some embodiments, a subset of that data is stored.

Figure 8:
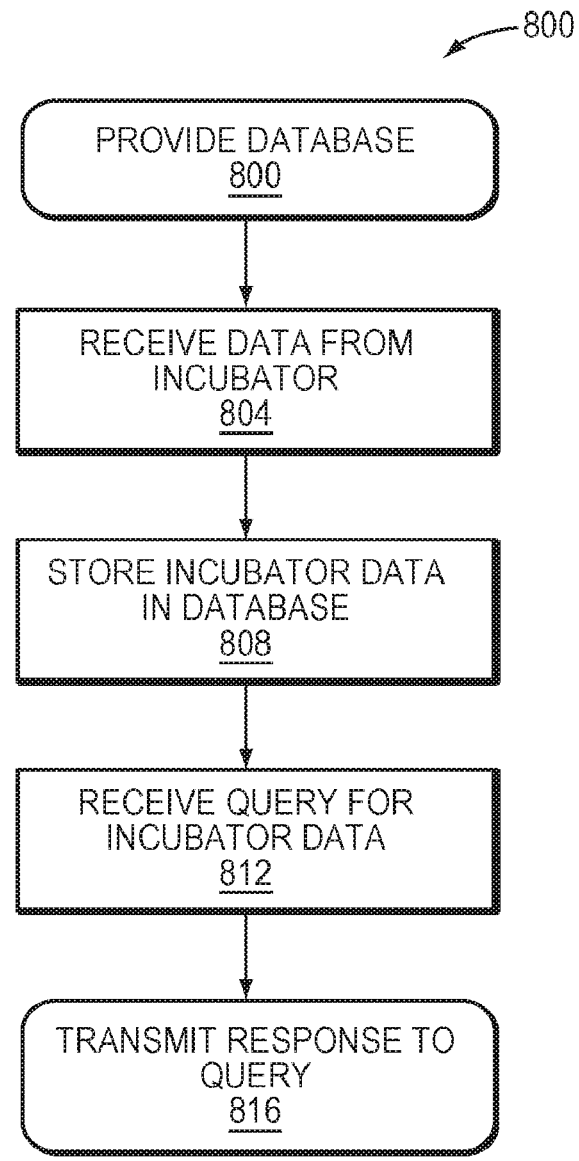
FIG. 8 depicts a flowchart of a method for operating a network-enabled cell culture incubator in accordance with one embodiment.

FIG. 8 depicts a flowchart describing an exemplary embodiment of a method 800 for operating a shared data repository as described herein. In this embodiment, a computing unit executes instructions stored on a non-transitory storage medium that, when executed, provide a database for storing various incubation related data sets (Step 800): protocols, protocol outcomes, protocol parameters, etc. The database itself may be structured (e.g., SQL, or object-oriented) or unstructured (e.g., Hadoop). The computing unit may be a single computing device or a plurality of interconnected computing devices.

The repository receives data from an incubator through a network interface (Step 804). The data may include various incubator related data sets: protocols, parameters for protocol operation, protocol results, images, etc.

Having received the incubator data, the repository stores the received data in the database (Step 808). In some embodiments, the data is anonymized prior to storage.

In further operation, the repository receives one or more requests for previously-stored incubator data via a network interface (Step 812). A request will typically include various parameters specifying the data of interest to facilitate retrieval of the data from the repository. The request may also include various security-related parameters that the repository may use to determine whether the requester is permitted to access the requested data.

Once the request is processed by the repository, the repository transmits the requested incubator data to the requester via a network interface (Step 816). Upon receipt, the requester typically uses the data to, e.g., configure, adjust, or execute one or more protocols on an incubator.

Figure 9:
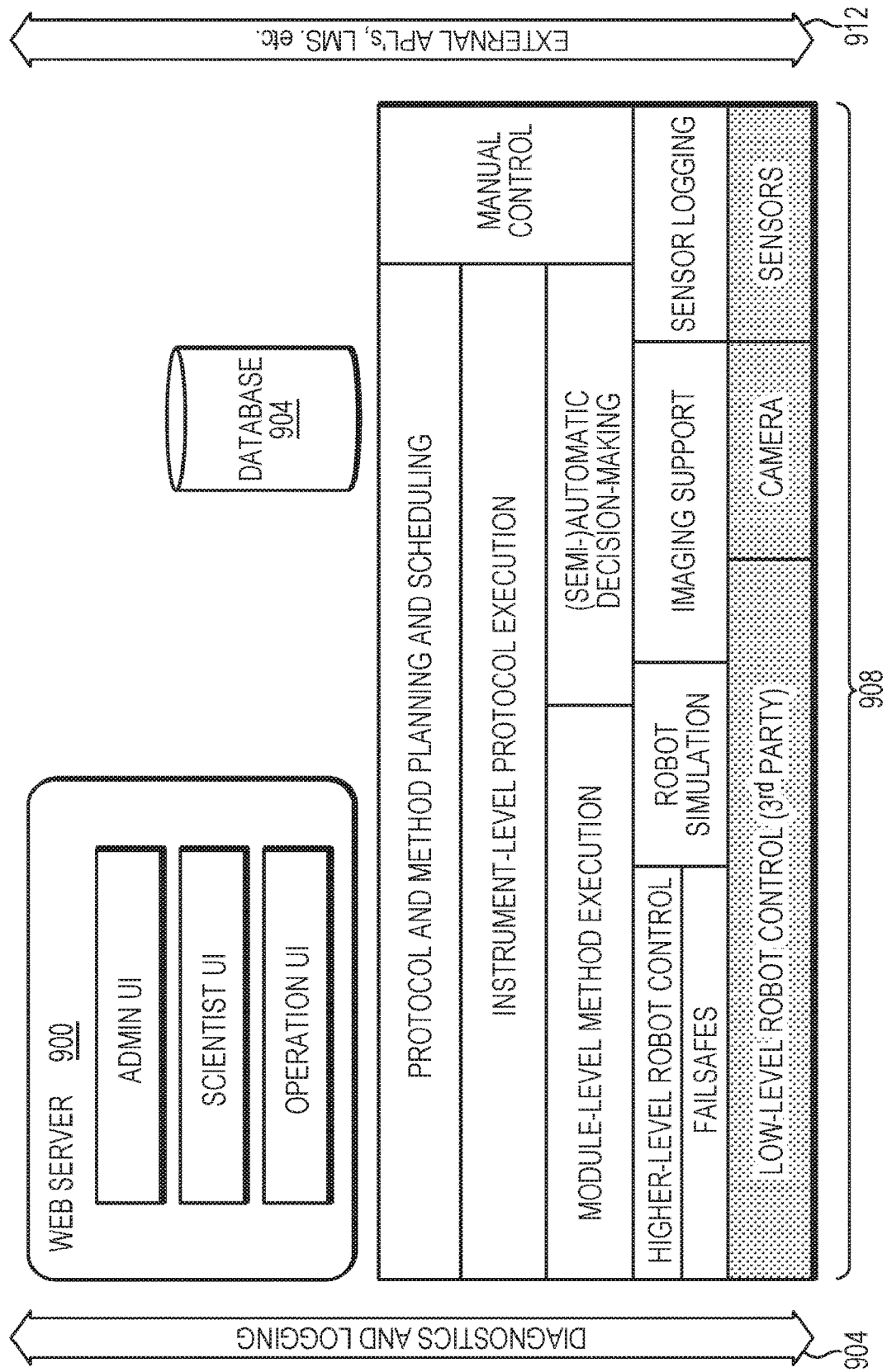
FIG. 9 is a software architecture diagram in accordance with one embodiment.

FIG. 9 presents a diagram representative of the software architecture used in various embodiments of the present invention. The incubator software architecture typically includes a web server 900 which is suitable for various operations 902, e.g., the presentation of information to an operator, the receipt of commands and parameters specified by an operator, the execution of applications for data processing and analysis, data logging, diagnostics, etc. In FIG. 9 the web server 900 is shown as presenting a variety of user interfaces (UI): a UI for use by an administrator, a UI for use by a scientist, a UI for use by the incubator operator, etc. Those user interfaces may be viewed by a user on a graphical display incorporated into the incubator, a graphical display on a device in communication with the incubator over a local network connection, a WAN connection, etc.

The architecture also includes one or more mechanisms for data storage, e.g., structured, unstructured, object-oriented, etc. These mechanisms are represented by database 904. These mechanisms may receive data originating locally with the incubator, data delivered over the network affecting the operation of the incubator, etc. These mechanisms may also be used as a source of data to be transmitted over the network for affecting the later occupation of the incubator or other incubator. The mechanisms for data storage may be stored completely or in part on the incubator itself, and may also incorporate data storage mechanisms stored on other computing resources, accessible via local or wide area network connection.

The software on the incubator 908 includes a variety of software components that operate to provide the functionality described above. These components are depicted in FIG. 9 as organized in various levels, with each level operating as an interface 912 to the components below it for the components above it.

The lowest level of the incubator software components 908 provide an interface to the various hardware components of the incubator: control of the robot portions of the incubator, an interface to the camera, an interface to the incubator sensors, etc.

The next level of modules 908 interact with the hardware interface components to implement various higher order functionalities. For example, the sensor logging module interfaces with the sensor modules to collect sensor data. The imaging support module interfaces with the camera module to collect and provide camera images to other software modules. The robot simulation, robot control, and failsafe modules interact with the robot control module to provide a set of well-defined operations that may be invoked by other software modules.

The higher level modules 908 in turn interact with these modules to implement the execution of protocols as discussed above: decomposing the protocols into various operations, scheduling and planning the execution of those operations, exposing an interface that allows a user to manually control the various operations of the incubator, etc.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, e.g., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, e.g., to mean including but not limited to.

Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method of facilitating a networked incubator operation, the method comprising:
providing an incubator connected to a network and configured with a cell imager therein;
automatically moving a cell culture vessel into a position wherein cells cultures within the vessel can be imaged;
automatically imaging the cell cultures to generate a plurality of images;
stitching the images together;
analyze the stitched together images to provide cell culture image analysis data;
communicating images and cell culture image analysis data from the incubator to the network;
storing the images and cell culture image analysis data in a database accessible to other devices connected to the network; and
using the image analysis data to predict cell growth and passaging time and to schedule imaging of the cells at the predicted passaging time.

2. The method of claim 1, further comprising receiving images and cell culture image analysis data at at least one of a laboratory information management system and an electronic lab notebook to provide a permanent record of cell culture operating parameters.

3. The method of claim 2, wherein the received at the at least one of a laboratory information management system and an electronic lab notebook further comprises at least one of a step in a process for incubator operation, temperature data, cell type data, time data, cell growth data, or growth medium data.

4. The method of claim 1, further comprising anonymizing images and cell culture image analysis data communicated to the network such that the networked incubator cannot be identified from the transmitted data.

5. The method of claim 1, wherein the networked incubator is further configured to analyze the stitched together images using deep learning.

6. The method of claim 1, wherein the networked incubator is further configured to analyze the stitched together images by detecting discrepancies between stem cells during cell development.

* * * * *